US00PP30867P2

(12) United States Plant Patent
Brown

(10) Patent No.: US PP30,867 P2
(45) Date of Patent: Sep. 3, 2019

(54) ***MANDEVILLA* PLANT NAMED 'KLEMS17026'**

(50) Latin Name: *Mandevilla sanderi*
Varietal Denomination: KLEMS17026

(71) Applicant: Klemm+Sohn GmbH & Co. KG, Stuttgart (DE)

(72) Inventor: Graham N. Brown, Pennant Hills (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,373

(22) Filed: Aug. 10, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

(56) References Cited

U.S. PATENT DOCUMENTS

PP29,893 P2 * 11/2018 Brown ..... A01H 6/088
Plt./232

* cited by examiner

*Primary Examiner* — Susan McCormick Ewoldt
*Assistant Examiner* — Karen M Redden
(74) *Attorney, Agent, or Firm* — Bethany Reid Roahrig; Cochran Freund & Young LLC

(57) ABSTRACT

A new *mandevilla* plant particularly distinguished by pink flowers and a vigorous upright growth habit, is disclosed.

1 Drawing Sheet

Genus and species: *Mandevilla sanderi.*
Variety denomination: 'KLEMS17026'.

BACKGROUND OF THE NEW PLANT

The present invention comprises a new and distinct variety of *mandevilla*, botanically known as *Mandevilla sanderi* and hereinafter referred to by the variety name 'KLEMS17026'. 'KLEMS17026' originated from a controlled cross in February 2010 in Cobbitty, New South Wales, Australia between the proprietary female *mandevilla* variety 'X08.12.6' (unpatented) and the proprietary male *mandevilla* variety 'No.2' (unpatented).

Seeds from the controlled cross were obtained and sown and plants were grown for evaluation. A single plant was selected in February 2012 in Cobbitty, New South Wales, Australia and subsequently named 'KLEMS17026'. In February 2012 'KLEMS17026' was first vegetatively propagated in Cobbitty, New South Wales, Australia by vegetative stem cuttings. 'KLEMS17026' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Cobbitty, New South Wales, Australia.

1. Pink flowers; and
2. Vigorous vining upright growth.

DESCRIPTION OF THE PHOTOGRAPH

This new *mandevilla* plant is illustrated by the accompanying photograph which shows an overall view of the plant.

The photograph is of an approximately 8 month-old plant grown in Latina, Italy, under greenhouse conditions, in September 2015. The colors shown are as true as can be reasonably obtained by conventional photographic procedures.

DESCRIPTION OF THE NEW VARIETY

The following detailed descriptions set forth the distinctive characteristics of 'KLEMS17026'. The data which define these characteristics were collected from asexual reproductions carried out in Cobbitty, New South Wales, Australia. Data was collected on 120 day old plants grown in Cobbitty, New South Wales, Australia in a greenhouse in October 2017. Color references are to The R.H.S. Colour Chart of The Royal Horticultural Society of London (R.H.S.), 5$^{th}$ edition (2007).

Classification:
- *Family.*—Apocynaceae.
- *Botanical.*—*Mandevilla sanderi.*
- *Common.*—*Mandevilla.*
- *Designation.*—'KLEMS17026'.

Parentage:
- *Female parent.*—The proprietary female *mandevilla* variety 'X08.12.6' (unpatented).
- *Male parent.*—The proprietary male *mandevilla* variety 'No. 2' (unpatented).

Plant:
- *Habit.*—Vigorous upright growth.
- *Height.*—100.0 cm.
- *Spread.*—30.0 cm.
- *Propagation type.*—Vegetative cuttings.
- *Time to produce a rooted young plant.*—8 weeks.

*Root description*.—Does not develop bulbs, corms, or rhizomes; root structure is ovate.
*Rooting habit*.—Normal.

Lateral branches:
*Number per plant*.—5.
*Branching habit*.—Moderate.
*Length*.—Approximately 60 cm.
*Diameter*.—0.4 cm.
*Internode length*.—Between 2.0 cm and 20.0 cm.
*Strength*.—Medium.
*Texture*.—Glossy, shiny, and no pubescence.
*Color*.—RHS 141D.

Foliage:
*Arrangement*.—Opposite.
*Length*.—About 5.0 cm.
*Width*.—About 3.0 cm.
*Shape*.—Composed.
*Apex*.—Cuspidate.
*Base*.—Obtuse.
*Margin*.—Entire.
*Texture*.—Upper surface: Glossy, no pubescence. Lower surface: Leathery and dull.
*Venation pattern*.—Pinnate.
*Venation color*.—Upper surface: RHS 141C. Lower surface: RHS 141C.
*Color of developing leaves*.—Upper surfaces: RHS 141A. Lower surface: RHS 141C.
*Color of fully expanded leaves*.—Upper surface: RHS 141A. Lower surface: RHS 141C.

Petioles:
*Length*.—About 2.0 cm.
*Diameter*.—About 0.2 cm.
*Texture*.—Smooth and dull.
*Color*.—Upper surface: RHS 141A. Lower surface: RHS 141C.

Inflorescence:
*Flower type and habit*.—Single.
*Natural flowering season*.—Spring, summer, and autumn.
*Lastingness of flowers on the plant*.—About 14 days.
*Fragrance*.—Absent.
*Flower appearance*.—Glossy.
*Flower diameter*.—About 5.0 cm.
*Flower length*.—About 4.0 cm.
*Throat diameter*.—2.5 cm.
*Tube length*.—3.0 cm.
*Tube diameter, at the base*.—0.5 cm.
*Number of flowers per inflorescence* (*typically observed*).—3.
*Inflorescence height*.—15 cm.
*Inflorescence diameter*.—15 cm.
*Number of flowers per plant*.—15.
*Peduncle*.—Length: 20.0 cm. Width: 0.3 cm. Texture: Smooth. Strength: Moderate. Luster: Shiny. Aspect: Erect. Color: RHS 141C.

Flower buds:
*Texture*.—Smooth.
*Luster*.—Shiny.
*Height*.—About 4.0 cm.
*Diameter*.—About 1.0 cm.
*Shape*.—Tall, cylindrical.
*Color*.—RHS N66C.

Corolla:
*Petal number per flower*.—5.
*Arrangement*.—Radial.
*Petal lobe length*.—2.0 cm.
*Petal lobe width*.—2.0 cm.
*Petal lobe shape*.—Round.
*Petal apex*.—Obtuse.
*Petal margin*.—Entire.
*Petal texture* (*both surfaces*).—Glossy, pubescence is sparse.
*Throat texture*.—Satiny.
*Tube texture*.—Satiny.
*Color of petal lobes when opening*.—Upper surface: RHS N66A. Lower surface: RHS N66C.
*Color of petal lobes when fully opened*.—Upper surface: RHS N66B. Lower surface: RHS N66C.
*Color of throat*.—RHS N63A.
*Color of tube*.—RHS 14A.

Sepals:
*Sepal luster* (*both surfaces*).—Dull.
*Arrangement*.—Fused at base.
*Number per flower*.—5.
*Length*.—2.0 cm.
*Width*.—0.3 cm.
*Shape*.—Lanceolate.
*Apex*.—Obtuse.
*Margin*.—Entire.
*Texture* (*both surfaces*).—Sparse pubescence.
*Color* (*both surfaces*).—RHS 155B.

Pedicels:
*Pedicel luster*.—Shiny.
*Length*.—2.0 cm.
*Diameter*.—0.3 cm.
*Surface texture*.—Smooth.
*Strength*.—Strong.
*Aspect*.—Erect.
*Color*.—RHS 52C.

Reproductive organs:
*Stamens*.—Quantity per flower: 5. Filament length: Less than 0.5 cm. Filament color: RHS 14D. Anther length: 0.1 cm. Anther color: RHS 14D. Pollen amount: Sparse. Pollen color: RHS 155A.
*Pistils*.—Quantity per flower: 1. Pistil length: 0.4 cm. Stigma shape: Ovate. Stigma color: RHS 145B. Style length: 0.1 cm. Style color: RHS 145C. Ovary color: RHS 138C.

Fruit and seed set: None observed.
Temperature tolerance: High tolerance to heat.
Disease and pest/insect resistance: None observed.

COMPARISON WITH PARENTAL LINES AND KNOWN VARIETY

'KLEMS17026' is distinguished from its parents as described in Table 1:

TABLE 1

Comparison with Parental Lines

| Characteristic | 'KLEMS17026' | Female parent 'X08.12.6' | Male Parent 'No. 2' |
|---|---|---|---|
| Flower size | Medium | Medium | Small |
| Plant height | Medium | Tall | Short |

'KLEMS17026' can be compared to the commercial varieties 'Sunparaprero' (U.S. Plant Pat. No. 19,399) and 'KLEMS16028' (U.S. Plant Pat. No. 29,893). Differences between the two varieties are described in Tables 2 and 3:

TABLE 2

Comparison with Similar Variety

| Characteristic | 'KLEMS17026' | Commercial line 'Sunmandecrim' |
|---|---|---|
| Vining | Medium | Strong |

TABLE 3

Comparison with Similar Variety

| Characteristic | 'KLEMS17026' | 'KLEMS16028' |
|---|---|---|
| Leaf Size | 5.0 cm in length; 3.0 cm in width | 4.0 cm in length; 2.0 cm in width |
| Peduncle Length | 20.0 cm | 6.0 cm |

I claim:

1. A new and distinct variety of *mandevilla* plant named 'KLEMS17026' as illustrated and described herein.

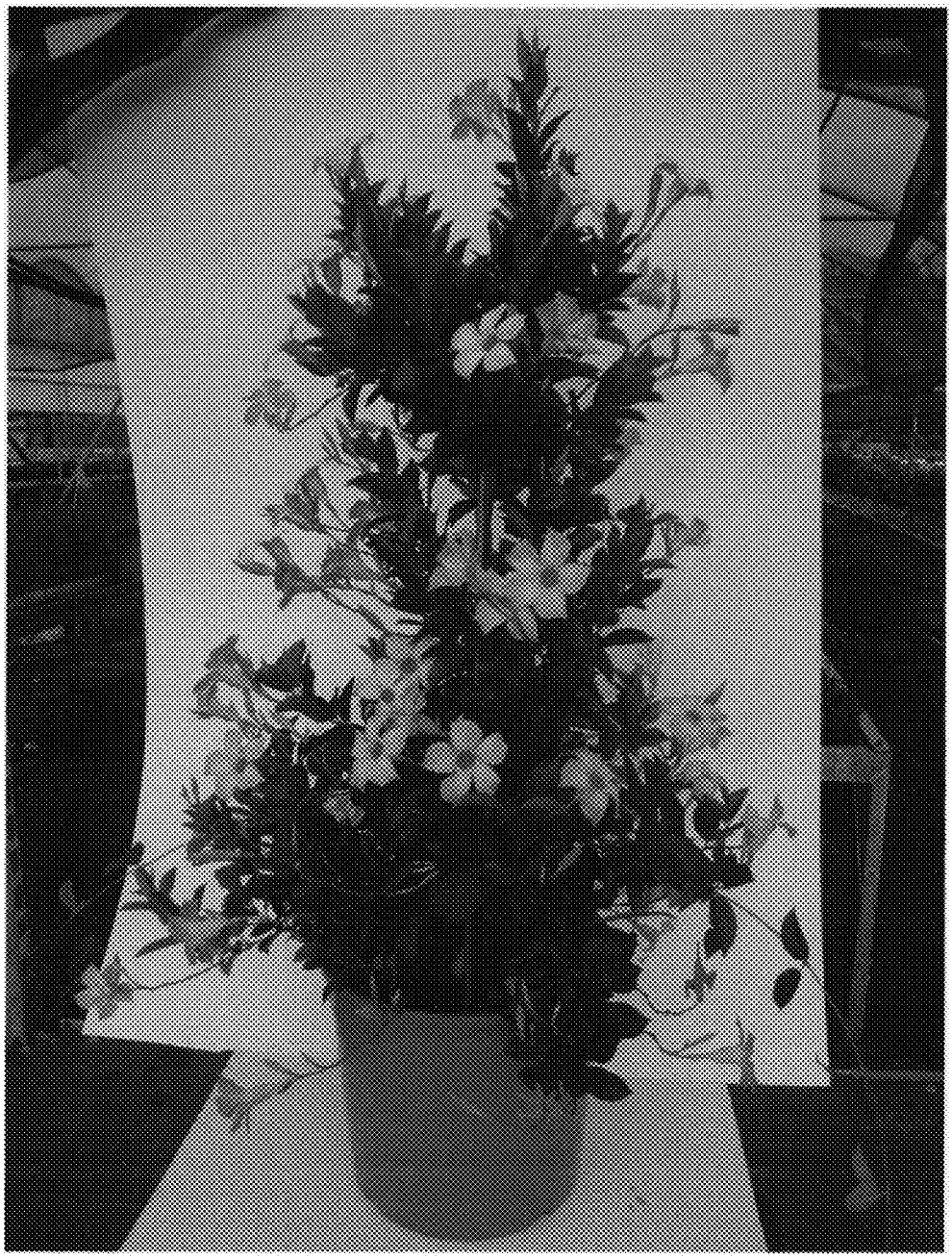

* * * * *